United States Patent
Van Dam et al.

(10) Patent No.: US 7,024,013 B1
(45) Date of Patent: Apr. 4, 2006

(54) SOUND REDUCTION/ELIMINATION DEVICE

(76) Inventors: Gregory A. Van Dam, 5610 W. Atlantic Ave., Apt. 202, Delray Beach, FL (US) 33484; James Padula, 4824 N. State Rd. #7, Coconut Creek, FL (US) 33073

( * ) Notice: Subject to any disclaimer, the term of this patent is extended or adjusted under 35 U.S.C. 154(b) by 207 days.

(21) Appl. No.: 10/754,590

(22) Filed: Jan. 12, 2004

(51) Int. Cl.
*H04R 25/00* (2006.01)

(52) U.S. Cl. ................ 381/376; 381/371; 381/374; 2/209

(58) Field of Classification Search ............ 381/309, 381/370, 371, 372, 374, 376–380, 383; 2/209, 2/906; 128/866, 867; 181/20, 128–130, 181/135
See application file for complete search history.

(56) References Cited

U.S. PATENT DOCUMENTS

| | | | |
|---|---|---|---|
| 2,501,107 A * | 3/1950 | Volkmann | 381/378 |
| 3,593,341 A | 7/1971 | Aileo | |
| 3,661,225 A * | 5/1972 | Anderson | 181/175 |
| 3,728,741 A | 4/1973 | Lepor | |
| 4,471,496 A | 9/1984 | Gardner et al. | |
| 4,546,215 A | 10/1985 | Ferraro | |
| 4,856,118 A | 8/1989 | Sapiejewski | |
| 5,551,090 A | 9/1996 | Thompson | |
| 5,704,069 A | 1/1998 | Andersson | |
| 6,353,938 B1 | 3/2002 | Young | |

\* cited by examiner

*Primary Examiner*—Huyen Le
(74) *Attorney, Agent, or Firm*—C. J. Husar

(57) ABSTRACT

A sound attenuating device including an earmuff-like headset with two earpieces that is adjustable to accommodate different sized heads and includes a removable headband sleeve that eliminates hair entanglement. Additionally, one of the earpieces is fixedly attached to an end of the headband while the second earpiece is removable to allow for the removal and replacement of a fitted cotton sleeve which covers the headband. The headband washable cotton sleeve prevents hair entanglement, provides protection related to health and sanitary issues and also provides an aesthetically pleasing appearance. In addition to the removable cotton sleeve for the headband, each of the earpieces is also provided with a removable fitted cotton cover. Each earpiece has a rigid support member that includes an attachment ring and an extension portion that is secured to the outer surface of the layer of silicone, on the opposite side of the layer of silicone, at its center, there is a spongy, sound-dampening foam layer adjacent thereto and covered with one of the fitted cotton sleeves referred to above. The fitted cotton covers include an opening slit for inserting the earpiece and an elastic band for securement to the earpiece. One of the earpieces can be permanently attached to the headband while the other earpiece is removable to allow the headband fitted cotton sleeve to be slipped over the free end of the headband before the second earpiece is attached thereto.

9 Claims, 2 Drawing Sheets

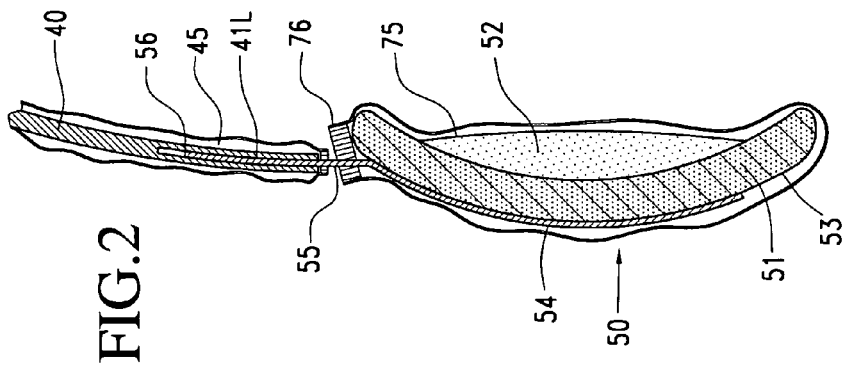
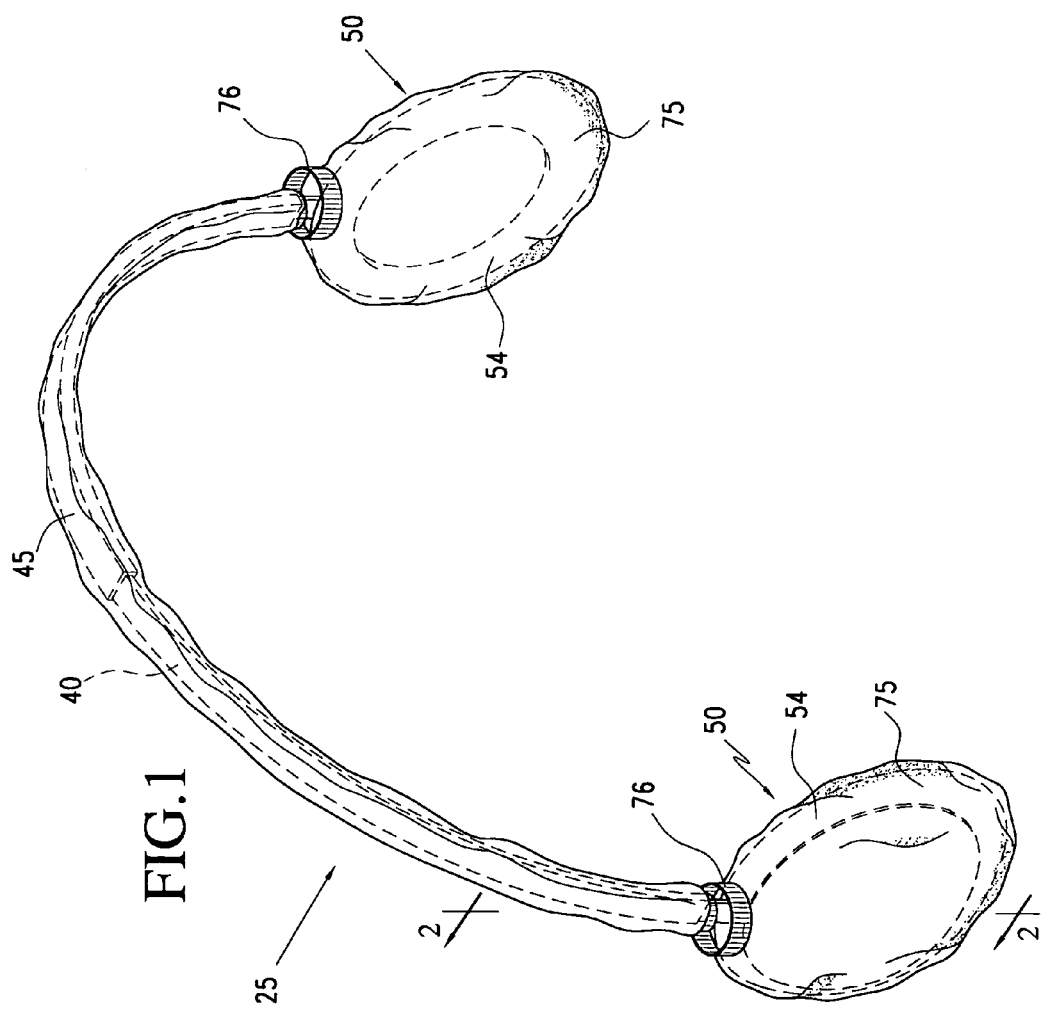

SOUND REDUCTION/ELIMINATION DEVICE

BACKGROUND OF THE INVENTION

The present invention relates to sound deadening devices and more particularly, it relates to an earmuff-like sound reduction/elimination device that can be worn primarily by individuals with sleep related problems that require total tranquility and silence to facilitate their having a good night's sleep or alternatively, block-out the snoring sounds of a sleeping partner. Applicant's intention was to provide a solution to this very serious problem. It is well known that people that live with snorers, usually get woken up by the snoring partner and in turn, wake up the snorer to try and get him to stop. This results in a potentially severe amount of sleep deprivation on the part of both parties. This problem can interfere with the longevity of a relationship, as well as interfere with the "victims" life, work, etc. That being said, this device would allow snorers and their partners to comfortably cohabit during sleeping hours, without being disturbed on either end by the snoring issue. Additionally, the subject sound eliminator has many daytime uses in addition to the aforementioned use as a sleeping aid. For example, it finds utility in any environment where the user desires to reduce/eliminate the sounds being heard, e.g. roaring engines while working around or on an aircraft, studying with deep concentration, etc.

The instant invention includes an earmuff-like headset that is adjustable to accommodate different sized heads and includes a removable headband sleeve that eliminates hair entanglement. Additionally, one of the earpieces is fixedly attached to an end of the headband while the second earpiece is removable to allow for the removal and replacement of a fitted cotton sleeve which covers the headband. The washable cotton sleeve prevents hair entanglement, provides protection related to health and sanitary issues and also provides an aesthetically pleasing appearance. In addition to the removable cotton sleeve for the headband, each of the earpieces is also provided with a removable fitted cotton cover. Each earpiece has a layer of silicone, and at its center, a spongy, sound-dampening foam layer adjacent thereto and covered with one of the fitted cotton covers referred to above. The fitted cotton covers include a slit opening for inserting the earpiece and an elastic band for securement on the earpiece. One of the earpieces can be permanently attached to the headband while the other earpiece is removable to allow the headband fitted cotton sleeve to be slipped over the free end of the headband before the second earpiece is attached thereto. It can readily be seen that the novel earpieces are sufficiently soft and pliable that they can be worn with great comfort since the total thickness of each earpiece is less than one-half inch.

DISCUSSION OF THE KNOWN PRIOR ART

A recent search of the Patent Office files in the appropriate Classes and subclasses revealed the following prior art documents U.S. Pat. No. 3,593,341 issued to J. A. Aileo on Jul. 20, 1971—discloses a pair of sound attenuating ear cups adapted for use with or without a safety helmet. As can be seen, the ear cups are thick units including a plastic shell and a pad of soft resilient material such as sponge plastic.

U.S. Pat. No. 3,728,741 issued to M. Lepor on Apr. 24, 1973—discloses a noise protective headgear that is worn over the ears and secured in place by a pair of drawstrings. The sound protection is provided with a fibrous glass blanket material encased in a tin-loaded vinyl with a soft rayon outer sheath U.S. Pat. No. 4,471,496—issued to Ross Gardner, Jr. et al on Sep. 18, 1984—discloses an articulated ear-to-headband connection. Additionally, it discloses earpieces that include an open-cell polymer foam that is backed by a rigid backwall.

U.S. Pat. No. 4,546,215—issued to Michael Ferraro on Oct. 8, 1985—discloses a pair of earmuffs and headband for use with a small portable radio. The disclosure relates primarily to the connection of the earmuff to the headband.

U.S. Pat. No. 4,856,118—issued to Roman Sapiejewski on Aug. 15, 1989—discloses a headphone cushioning system comprised of a pair of concentric rings of non-liquid gelatin-like silicone on a layer of soft, slow recovery foam enclosed in a thin stretchable layer of polyurethane skin. As noted in the drawings, the center of the device is an opening 12 through which sound is transmitted from the headphone transducer (not shown) to the ear of the wearer. Further, this patent utilizes a recovery foam with vent openings, while the subject application uses sound dampening foam. Applicant's sound dampening foam not only provides comfort to the wearer, but also, when combined with the silicone layer, plays an intricate role in facilitating sound elimination. Further, it appears that the patentee's primary object is to provide a comfortable earpiece while providing a good acoustic seal is a secondary goal.

U.S. Pat. No. 5,551,090—issued to Janet M. Thompson on Sep. 3, 1996—discloses an ear protecting apparatus for protecting children from noisy environments. The apparatus comprises a pair of earmuffs attached to a headband and made of noise attenuating foam material, such as foam rubber or neoprene.

U.S. Pat. No. 5,704,069—issued to Lars-Gunmar Anderson on Jan. 6, 1998—discloses a moisture absorbent cover for an earmuff. Its related to the problem of sweat and moisture at the sealing rings of earmuffs and is designed to overcome that problem.

U.S. Pat. No. 6,353,938—issued to Stephen F. Young on Mar. 12, 2002—discloses a sound attenuating earmuff comprised of rigid outer plastic cups that are provided with inner foam cups and an outer cushion and connected to a headband.

SUMMARY OF THE INVENTION

As can be seen from a review of the above-noted patents, none of the art discloses the combination of features embodied in applicant's novel earmuff sound reduction/elimination device. Various patents disclose individual features of the subject invention. However, no one document discloses individually adjustable earpieces, individual covers for the earpieces and a cover for the adjustable headband. Additionally, none of the prior art discloses the unique arrangement of a silicone layer and a foam layer followed by a fitted soft cotton cover for the individual earpieces and also a fitted sleeve for the headband. The arrangement of these components results in an earpiece that is less than ½ of an inch thick and allows for comfortable wearing as it contours itself to the ear. Further, none of the cited art discloses a headband that is adjustable two ways, i.e. in width to compensate for heads of different width and also a height adjustment to accommodate persons with different vertically shaped heads. Additionally, none of the prior art devices include a disclosure of the headband and earpiece rigid support members made out of a soft, pliable plastic or rubber for wearer comfort.

OBJECTS OF THE INVENTION

An object of the invention is to provide a sound attenuating device that includes an adjustable headband to accommodate different sized heads.

A further object of the invention is to provide a sound attenuating device with at least one removable earpiece to allow for installation of a fitted cotton sleeve over the headband to prevent hair entanglement.

A still further object of the invention is to provide a sound attenuating device that includes a fitted cotton cover for each earpiece.

Another object of the invention is to provide a supporting member for each earpiece to allow each earpiece to be connected to the headband.

Yet another object of the invention is to provide a sound attenuating device wherein each earpiece includes a center of silicone material followed by a spongy, sound dampening foam that significantly limits the noises received by the each ear.

A further object of the invention is to provide a sound attenuating device that includes a pair of earpieces that are approximately ½ inch thick, allowing for great comfort while sleeping.

These and other objects of the invention will become more apparent hereinafter. The instant invention will now be described with reference to the accompanying drawings wherein like reference characters designate the corresponding parts throughout the several views.

BRIEF DESCRIPTION OF THE DRAWINGS

FIG. 1 is a perspective view of the novel sound attenuating device with a pair of earpieces and headband with their respective fitted cotton covers and sleeve.

FIG. 2 is sectional view taken along the plane 2—2 of FIG. 1 illustrating details of the earpiece and it connection to the headband end.

DETAILED DESCRIPTION OF THE DRAWINGS

Figure 3:
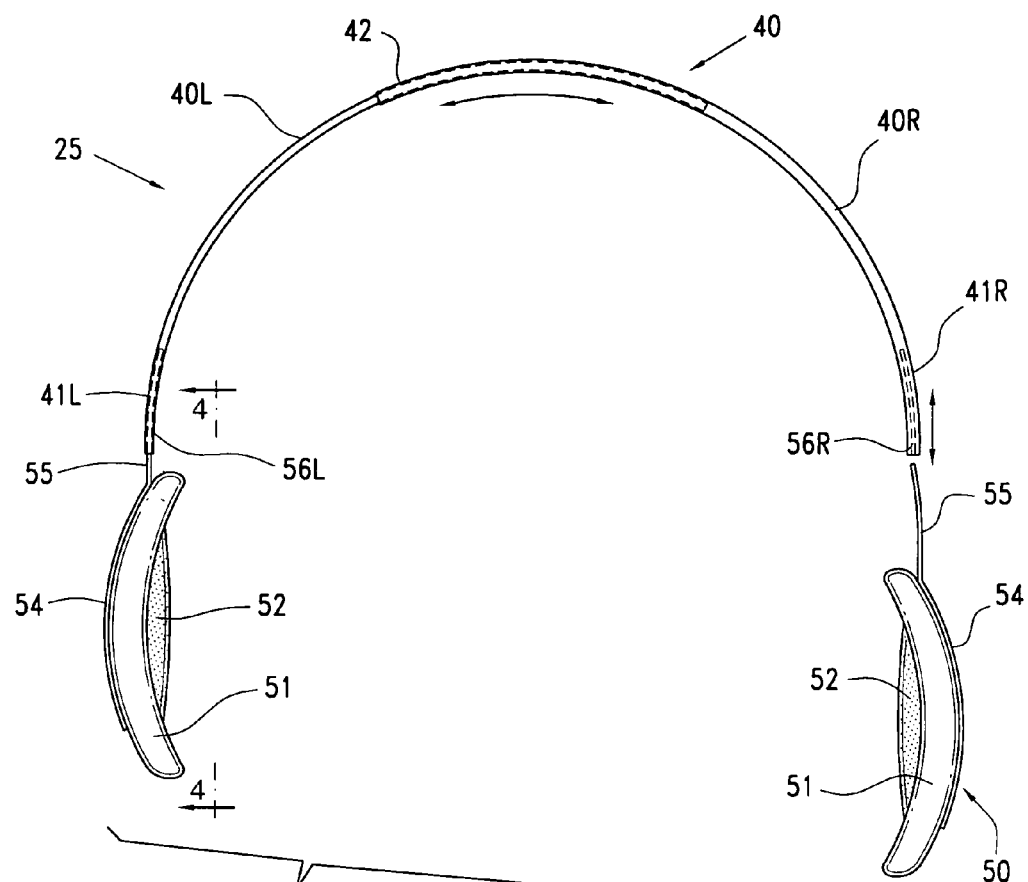
FIG. 3 is a frontal view of the sound attenuating head set without the fitted cotton sleeve on the headband or the earpiece covers.

FIG. 1, is a perspective view of the novel sound attenuating device indicated generally by reference numeral 25 with a pair of earpieces 50 attached to opposite ends of headband 40. As shown, headband 40, formed of soft plastic to provide a comfortable feeling while worn, and is covered with a washable fitted cotton sleeve 45 to prevent hair entanglement when worn. Additionally, each earpiece 50 is also provided with a fitted cotton cover 75 that has aesthetically pleasing design prints thereon and includes an elastic neck portion 76 that can be stretched to allow covers 75 to be pulled over their respective earpieces 50.

Referring now to FIG. 2, there is shown a sectional view taken along the plane 2—2 of FIG. 1. As illustrated, earpiece 50 comprises a molded silicone layer 51 with a spongy, sound-dampening foam layer 52 attached to the center thereof to add to the sound-dampening qualities of silicone layer 51. Each earpiece 50 is provided with a washable cotton fitted cover 75 that further adds to the sound-dampening qualities of the device and also provides an aesthetically pleasing appearance. As shown here, earpiece 50 is concave in shape, allowing the ear to be enclosed by each earpiece 50. The approximate dimensions of each earpiece 50 is 2½ inches wide and 3 inches in height with a total thickness of less than ½ inch thus allowing great comfort when worn while sleeping. Secured to the outer surface portion 53 of earpiece 50 is circular rigid support member 54, made of soft plastic to provide a comfortable feeling while worn, that includes an extension portion 55 at the top thereof and is received in slot 56 in the lowermost ends 41L, 41R of headband 40 where it is frictionally retained until it is desired to readjust for another user's head.

Turning now to FIG. 3, there is shown a perspective view of the sound attenuating device 25, without earpiece covers 75 or headband sleeve 45 in place, with one earpiece extension 55 received in opening 56L of end 41L of left headband portion 40L and the other earpiece extension portion 55 aligned with the opposite end 41R of headband portion 40R after its removal therefrom in preparation for the installation of fitted cotton headband sleeve 45. As shown, extension members 55 readily conform to the curvature of end portions 41L and 41R when inserted into headband openings 56L and 56R Additionally, headband size adjuster 42 is shown located in the center of headband 40 with left headband member 40L received in right headband member 40R where the headband members 40L, 40R are frictionally held until there is a need to readjust for a different sized head.

Figure 4:
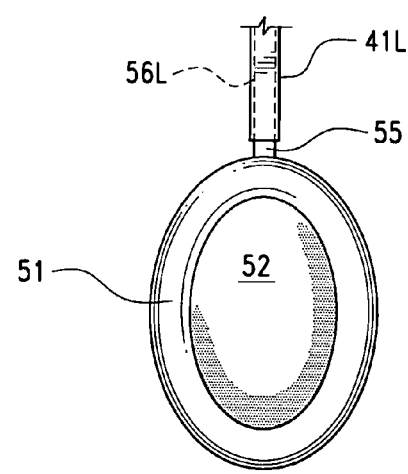
FIG. 4 is a side view of the left earpiece of FIG. 3, looking in the direction of arrows 4—4.

Referring now to FIG. 4, there is shown the view seen when looking in the direction of arrows 4—4 of FIG. 3. As indicated above, earpiece 50 does not have its fitted cotton cover 75 in place over earpiece 50 and therefore, centrally located spongy foam 52 is shown with silicone layer 51 extending therebeyond. Also, extension portion 55 of attachment member 54 is shown extending into opening 56L of left headband portion 41L.

While the invention has been described in its preferred embodiment, it is to be understood that the words which have been used are words of description rather than words of limitation and that changes may be made within the purview of the appended claims without departing from the full scope or spirit of the invention. Accordingly, the present invention is to be limited only by the appended claims, and not by the foregoing specification.

Having thus described our invention, We claim:

1. A sound attenuating apparatus for reducing the sound heard by individuals when sleeping, studying or any time it is desirous to reduce noise levels, said sound attenuating apparatus comprising:

an arcuate headband having a pair of opposite ends with size adjustment means located therebetween;

each of said ends of said headband having sound attenuating means mounted thereon;

said sound attenuating means comprising a pair of earmuffs with one of said earmuffs permanently attached to one end of said headband and the other of said earmuffs removably attached to the opposite end of said headband;

each of said earmuffs including a rigid support member having an extension connector portion for attachment to said ends of said headband and a circular portion for supporting and biasing said sound attenuating means toward one's ears when worn;

each of said headband and said rigid support members being formed of soft plastic to provide a comfortable feeling while worn;

each of said headband and said pair of sound attenuating earmuffs having removable covers that provide a measure of health protection, prevent hair entanglement with said headband and provide an overall aesthetically pleasing appearance to said sound attenuating apparatus;

each of said earmuffs further comprising a first layer of sound dampening silicone followed by a centrally located second layer of spongy, sound-dampening foam bonded thereto with said cover thereover, said first and second layers and said cover contributing to maximum sound reduction when worn by a user;

said headband, removable covers and said sound attenuating means having a combined total thickness of less than one-half inch and provide a comfortable fit over the ears and head of a user when worn.

2. A sound attenuating apparatus of the type defined in claim 1 wherein said circular portion and said extension connector portion of said rigid support members are made of a thin soft plastic material.

3. A sound attenuating apparatus of the type defined in claim 1 wherein said sound dampening silicone layer and said second layer of spongy, sound-dampening foam are adhesively bonded to said rigid support member.

4. A sound attenuating apparatus of the type defined in claim 1 wherein said headband size adjustment means comprises first and second headband members with one of said members having a slot therein and the other of said members sized to fit into said slot with cooperating frictional surfaces that will lock said headband members in their desired positions and retain them there until readjusted.

5. A sound attenuating apparatus of the type defined in claim 1 wherein each of said earmuffs includes a central concave portion with said spongy sound-dampening foam for comfortable fitting over the ear and providing an additional seal from exterior noise.

6. A sound attenuating apparatus of the type defined in claim 5 wherein each of said earmuffs is biased into close contact with the wearer's ears by said rigid support members.

7. A sound attenuating apparatus of the type defined in claim 6 wherein said circular portion of said rigid support member is embedded in said silicone layer with said extension portion integrally formed thereon and protruding from said silicone layer and receivable by a portion of said headband.

8. A sound attenuating apparatus of the type defined in claim 1 wherein said covers are washable, fitted cotton covers that include an elastic neck portion so it can be stretched and retained on said earmuffs and readily be removed for laundering and replacement.

9. A sound attenuating apparatus of the type defined in claim 8 wherein said fitted cotton covers have aesthetically pleasing design prints thereon.

\* \* \* \* \*